United States Patent
Herschman (12)

(10) Patent No.: US 9,220,829 B2
(45) Date of Patent: Dec. 29, 2015

(54) IMPLANTABLE SYSTEMS AND METHODS FOR REMOVING SPECIFIC IMPURITIES FROM FLUIDS SUCH AS BLOOD

(76) Inventor: Zvi Herschman, West Hempstead, NY (US)

( * ) Notice: Subject to any disclaimer, the term of this patent is extended or adjusted under 35 U.S.C. 154(b) by 494 days.

(21) Appl. No.: 13/044,147

(22) Filed: Mar. 9, 2011

(65) Prior Publication Data

US 2012/0232458 A1 Sep. 13, 2012

(51) Int. Cl.
*A61F 2/04* (2013.01)
*B01D 61/42* (2006.01)
*A61M 1/16* (2006.01)
*A61F 2/02* (2006.01)
*A61M 1/34* (2006.01)
(Continued)

(52) U.S. Cl.
CPC .............. *A61M 1/1678* (2013.01); *A61F 2/022* (2013.01); *A61M 1/3417* (2014.02); *A61F 2230/0069* (2013.01); *A61F 2250/0024* (2013.01); *A61F 2250/0043* (2013.01); *B01D 57/02* (2013.01); *B01D 61/422* (2013.01); *B01D 61/425* (2013.01); *B01D 61/44* (2013.01); *B01D 61/46* (2013.01); *B01D 61/52* (2013.01); *B01D 61/54* (2013.01)

(58) Field of Classification Search
CPC ....... A61F 2/022; A61M 1/16; A61M 1/1609; A61M 1/1619; A61M 1/1625; A61M 1/1633; A61M 1/1678; A61M 1/34; A61M 1/3417
USPC ........ 623/23.65; 604/57, 4.01–6.16; 977/904, 977/925, 931; 600/29; 204/518–520, 527, 204/540, 543, 554–573, 627–628
See application file for complete search history.

(56) References Cited

U.S. PATENT DOCUMENTS 3,994,799 A * 11/1976 Yao et al. ..................... 604/5.04
5,489,370 A 2/1996 Lomasney et al.
(Continued)

FOREIGN PATENT DOCUMENTS

EP 2087916 A1 8/2009
EP 2446908 A1 5/2012
(Continued)

OTHER PUBLICATIONS

Bonsor et al. "How Nanotechnology Works". HowStuffWorks.com. Downloaded from <http://science.howstuffworks.com/nanotechnology2.htm/printable> on Dec. 31, 2014.*
(Continued)

*Primary Examiner* — Andrew Iwamaye
(74) *Attorney, Agent, or Firm* — Wiggin and Dana LLP

(57) ABSTRACT

Systems and methods utilize semipermeable nanotubes in conjunction with application of controlled electrical potentials across semipermeable nanotube walls allow selective transport of charged impurities (e.g., charged impurities, ions, etc.) from a fluid into these nanotubes. Impurities collected in these nanotubes can then be removed from the fluid, (e.g., blood) as a waste stream. A collection of semipermeable nanotubes each carrying a waste stream can be aggregated and merged into a ureter for excretion thereby providing an artificial kidney system. Sensors that detect/measure various impurities may be included in the system to feed information to a microprocessor to inform on concentrations of impurities, and thereby control electrical potentials applied to the system.

13 Claims, 8 Drawing Sheets

(51) Int. Cl.
  *B01D 61/46* (2006.01)
  *B01D 61/44* (2006.01)
  *B01D 61/52* (2006.01)
  *B01D 61/54* (2006.01)
  *B01D 57/02* (2006.01)

(56) References Cited

U.S. PATENT DOCUMENTS

| | | | |
|---|---|---|---|
| 5,776,325 A | | 7/1998 | Partridge |
| 6,086,739 A | | 7/2000 | Hodko |
| 6,284,117 B1 | * | 9/2001 | Smolko et al. ............. 204/543 |
| 6,555,058 B2 | | 4/2003 | Kamibayashi et al. |
| 7,048,856 B2 | | 5/2006 | Fissell, IV et al. |
| 7,066,900 B2 | | 6/2006 | Botto et al. |
| 7,540,963 B2 | | 6/2009 | Fissell, IV et al. |
| 7,651,600 B2 | | 1/2010 | Han et al. |
| 8,871,074 B2 | * | 10/2014 | Suh et al. .............. 204/674 |
| 2004/0049288 A1 | * | 3/2004 | Levin .................. 623/23.65 |
| 2004/0124147 A1 | * | 7/2004 | Fissell et al. ............. 210/650 |
| 2005/0103622 A1 | * | 5/2005 | Jha et al. ................ 204/237 |
| 2006/0027499 A1 | * | 2/2006 | Ajayan et al. ............ 210/636 |
| 2006/0073089 A1 | * | 4/2006 | Ajayan et al. ........... 423/447.2 |
| 2006/0240061 A1 | * | 10/2006 | Atala et al. ............. 424/422 |
| 2007/0108068 A1 | * | 5/2007 | Suh et al. ............... 205/766 |
| 2008/0004712 A1 | | 1/2008 | Humes et al. |
| 2008/0051696 A1 | * | 2/2008 | Curtin et al. ............. 604/29 |
| 2008/0107739 A1 | | 5/2008 | Kraft |
| 2008/0223795 A1 | | 9/2008 | Bakajin et al. |
| 2009/0131858 A1 | * | 5/2009 | Fissell et al. ............. 604/57 |
| 2010/0100027 A1 | | 4/2010 | Schilthuizen et al. |
| 2010/0316694 A1 | * | 12/2010 | Mousa et al. ............. 424/443 |
| 2011/0247937 A1 | * | 10/2011 | Suh et al. .............. 204/554 |
| 2012/0211367 A1 | * | 8/2012 | Vecitis ................. 204/554 |

FOREIGN PATENT DOCUMENTS

| | | | | |
|---|---|---|---|---|
| WO | WO 2008075951 A1 | * | 6/2008 | ............. A61M 1/36 |
| WO | 2008086477 A1 | | 7/2008 | |

OTHER PUBLICATIONS

TheNanoAge. "Carbon Nanotubes". TheNanoAge.com. Downloaded from <http://www.thenanoage.com/carbonnanotubes.htm>. On Dec. 31, 2014.*

Allen R. Nissenson et al., The Human Nephron Filter: Toward a Continuously Functioning, Implantable Artificial Nephron System, May 20, 2005, Blood Purification, vol. 23, pp. 269-274, USA.

H. M. Amasha et al., Implantable Electronic Kidney, IFMBE Proceedings, vol. 5, Track 18, p. 3172, USA.

International Search Report, corresponding to International Application No. PCT/US2012/28018, mailed Jun. 19, 2012.

William Fissell, Anna Dubnisheva, Abigail Eldridge, Aaron Fleischman, Andrew Zydney and Shuvo Roy; High Performance Silcon Nanopore Hemofiltration Membranes, National Institute of Health, J. Memb Sci. Jan. 5, 2009.

A.T. Conlisk, Subhra Datta, William Fissell and Shuvo Roy; Biomolecular Transport Through Hemofiltration Membranes, National Institute of Health, Ann Biomed Eng. Apr. 2009.

Chad D. Vecitis et al, "Electrochemical Carbon Nanotube Filter for Adsorption, Desorption, and Oxidation of Aqueous Dyes and Anions," Journal of Physical Chemistry, Feb. 16, 2011, pp. 3621-3629, vol. 115, No. 9.

Supplemental European Search Report in EP Application No. 12755026.7 dated Mar. 11, 2015.

* cited by examiner

IMPLANTABLE SYSTEMS AND METHODS FOR REMOVING SPECIFIC IMPURITIES FROM FLUIDS SUCH AS BLOOD

FIELD

Systems and methods are disclosed for removing impurities, including water, from fluids, including bodily fluids such as blood, by causing electric field induced transport of selected impurities such that they can be readily captured within semipermeable nanotubes and/or removed as a stream of waste species.

BACKGROUND

Typically, in healthy humans and animals, their body's kidneys, amongst other organs, effectively remove excess water, salts, and toxins as well as breakdown materials, such as, proteins and other waste products (e.g., produced by metabolism) circulating in blood. Nearly 400,000 people in the United States of America, and as many as two million people worldwide suffer from kidney failure. This number is estimated to be increasing at annual rates of about 9%. In these individuals, their own kidney does not function properly and naturally produced wastes are not effectively removed.

Generally speaking, to restore such a patient to close to full health, a kidney transplant is needed. However, the present demand for kidney transplants is heavily outnumbered by the limited supply of donor organs. For example, as of 2011 there are about 85,000 patients in the United States of America on waiting lists for a kidney, while only about 17,000 kidney transplants took place in 2010. Even with a kidney transplant, complications such as host rejection and complications from immunosuppressive medications, which can be required to be taken for life to prevent rejection, is not uncommon. In addition, graft versus host and transplanted infectious diseases can also develop. Hence, in many patients with loss of kidney function (e.g., renal failure), the normal kidney cleaning process has to be performed artificially, for example, through external treatments such as dialysis, typically either hemodialysis or peritoneal dialysis.

In hemodialysis, for example, a patient's blood is typically re-routed outside the body to a dialyzer which filters the blood using disposable cartridges that include numerous substantially small, semipermeable, plastic membranes, with varying pore sizes. Using this technique, as blood diffuses through these membranes, contaminates are removed from the patient's blood in conjunction with a counter-current flow of a fresh dialysate solution. Toxins in the blood (e.g., salts and various unwanted low molecular weight molecules) preferentially diffuse across these membranes as a result of flow-induced or osmotic pressure differentials, resulting in reduced toxin concentrations. The now purified blood is then returned to the patient's body, usually via a vein in the arm and/or through the lumen of an inserted catheter.

While undergoing dialysis, patients are required to be connected to substantially large and expensive machines. For example, patients may typically be required to receive treatments at least three to four times a week, for about three to five hours at a time. Even then, dialysis machines may only be about 13% as effective as a fully functional kidney. Five-year survival rates of patients on dialysis has been estimated to be just 33-35%.

Further, when using dialysis, only about 10-40% of larger molecules, called middle molecular weight molecules, are removed during a given dialysis session. The ability to remove large molecular mass molecules merely by diffusion across a membrane is substantially decreased. This can lead to a buildup of larger-sized toxins within the patient's blood. Consequently, without removal, these toxins can reach abnormally high concentration levels and can damage the body over time. Some have speculated that inefficient removal of these toxins represents a significant limitation of current renal dialysis technology.

To achieve adequate removal of these toxins, manufactures and nephrologists have been attempting to increase surface areas of dialysis membranes and also prolong dialysis treatment times. However, there are limits to increasing surface areas of dialysis membranes. In addition, increased dialysis times coupled with the physical and social side effects of dialysis, can reduce the patient's quality of life and add prohibitive expense to people suffering from a loss of kidney function.

SUMMARY

In exemplary embodiments, systems for removing impurities from a fluid can comprise at least one semipermeable nanostructure assembly that can have a plurality of pores through which at least some of the impurities may be transported. The system for removing impurities from fluids can also comprise an enclosure(s) that can contain the at least one semipermeable nanostructure assembly and/or the enclosure (s) can provide a fluid path through which at least some of the fluid may flow. Further, an electric field can be generated, for example, to transport at least some of the impurities in the fluid through the plurality of pores in the at least one semipermeable nanostructure assembly, thereby removing those impurities from the fluid.

In exemplary embodiments, at least some of the impurities removed from the fluid can be (i) captured within the at least one semipermeable nanostructure assembly and/or (ii) removed from the system as a waste stream.

In exemplary embodiments, the at least one semipermeable nanostructure assembly can further comprise a plurality of semipermeable nanostructures assembled, for example, forming array(s). In some instances, at least some of the plurality of semipermeable nanostructures forming the array (s) can be aligned substantially in parallel.

In exemplary embodiments, the at least one semipermeable nanostructure assembly can further comprise nanotube(s).

In exemplary embodiments, the system can further comprise sensor(s) that can monitor the amount of at least one impurity within the fluid. Also, in exemplary embodiments, the system can further comprise microprocessor(s) that can regulate the electric field by, for example, analyzing information that may be obtained from the sensor(s).

In exemplary embodiments, the sensor(s) can utilize an electrochemical and/or optical detection system. In some instances, the electric field can be generated by a fixed and/or variable voltage waveform. Also, in some instances, the microprocessor(s) can utilize the output from sensor(s) to adjust the electric field, for example, in accordance with the monitored impurity level.

In exemplary embodiments, the at least one semipermeable nanostructure assembly can be constructed from materials comprising carbon, polymers, cross-linked polymers, inorganic compounds, inorganic polymers, metals, and/or organic compounds.

In exemplary embodiments, the plurality of pores can be dimensioned to allow passage of specific impurities.

In exemplary embodiments, an artificial kidney system for removing impurities from bodily fluids can comprise at least one semipermeable nanostructure assembly that can have a plurality of pores through which at least some of these impurities may be transported. The artificial kidney system can also include an enclosure(s) that can contain the at least one semipermeable nanostructure assembly and/or the enclosure(s) that can provide a fluid path through which at least some of the bodily fluid may flow. Further, an electric field can be generated to, for example, transport at least some of the impurities in the bodily fluid through the plurality of pores in the at least one semipermeable nanostructure assembly, thereby removing those impurities from the bodily fluid.

In exemplary embodiments, the bodily fluid can be blood.

In exemplary embodiments, at least some of the impurities removed from the bodily fluid can be (i) captured within the at least one semipermeable nanostructure assembly and/or (ii) removed from the system as a waste stream.

In exemplary embodiments, the at least one semipermeable nanostructure assembly can further comprise a plurality of semipermeable nanostructures assembled, for example, forming array(s). In some instances, at least some of the plurality of semipermeable nanostructures forming the array(s) can be aligned substantially in parallel.

In exemplary embodiments, the at least one semipermeable nanostructure assembly can further comprise nanotube(s).

In exemplary embodiments, the artificial kidney system can further comprise sensor(s) that can monitor the amount of at least one impurity within the bodily fluid.

In exemplary embodiments, the artificial kidney system can further comprise microprocessor(s) that can regulate the electric field by, for example, analyzing information that may be obtained from sensor(s). In some instances, the sensor(s) can utilize electrochemical and/or optical detection. Also, in some instances, the electric field can be generated by a fixed and/or variable voltage waveform. In exemplary embodiments, the microprocessor(s) can utilize the sensor(s) to adjust the electric field, for example, in accordance with the monitored impurity level.

In exemplary embodiments, the bodily fluid to be purified can enter the system from an artery and/or a vein and/or can exit the system by flowing to the same artery, a different artery, the same vein, and/or a different vein.

In exemplary embodiments, the electric field can be generated by an energy source that can be (i) an implanted battery and/or (ii) a biological fuel cell utilizing glucose potential gradients normally occurring in blood.

In exemplary embodiments, the at least one semipermeable nanostructure assembly can be constructed from materials comprising carbon, polymers, cross-linked polymers, inorganic compounds, metals, and/or organic compounds.

In exemplary embodiments, one or more anticoagulants can be attached to one or more surfaces of the system that contact the bodily fluid.

In exemplary embodiments, the plurality of pores can be dimensioned to pass water and/or impurities while red blood cells and/or other large blood constituents can be excluded.

In exemplary embodiments, the artificial kidney system can be configured and/or dimensioned to be implantable with a human body.

In exemplary embodiments, methods for removing impurities from fluids can comprise the steps of providing at least one semipermeable nanostructure assembly that can have a plurality of pores through which at least some of the impurities can be capable of being transported. The methods for removing impurities from a fluid can also comprise the step of providing a fluid path through which at least some of the fluid flows along the at least one semipermeable nanostructure assembly. Further, the methods for removing impurities from fluids can comprise the step of generating an electric field, for example, to transport at least some of the impurities in the fluid through the pores of the at least one semipermeable nanostructure assembly, thereby removing those impurities from the fluid in the fluid path.

In exemplary embodiments, the method can further comprise collecting the impurities transported through the pores of the at least one semipermeable nanostructure assembly to form a separate waste stream.

In exemplary embodiments, the step of providing at least one semipermeable nanostructure assembly can further comprise the step of providing a plurality of semipermeable nanostructures and/or assembling the plurality of semipermeable nanostructures, for example, to form array(s).

In exemplary embodiments, the at least one semipermeable nanostructure assembly can further comprise nanotube(s).

In exemplary embodiments, the method can further comprise the step of providing sensor(s) to, for example, monitor the impurities that can be transported by the electric field through the at least one semipermeable nanostructure assembly. In some instances, the method can further comprise the step of regulating the electric field by analyzing information that may be obtained from the sensor(s). Further, in some instances, the step of regulating the electric field can further comprise the step of regulating the electric field by using a fixed and/or variable voltage waveform.

In exemplary embodiments, the method can further comprise the step of adjusting the electric field in accordance with the detected monitored impurity levels.

In exemplary embodiments, the method can further comprise the step of dimensioning the plurality of pores to pass specific impurities.

In exemplary embodiments, the method can further comprise the step of attaching one or more anticoagulants to one or more surfaces that contact the bodily fluid.

BRIEF DESCRIPTION OF DRAWINGS

The features and advantages of the disclosure will be more fully understood with reference to the following description, when taken in conjunction with the accompanying figures, wherein.

DETAILED DESCRIPTION

Figure 1:
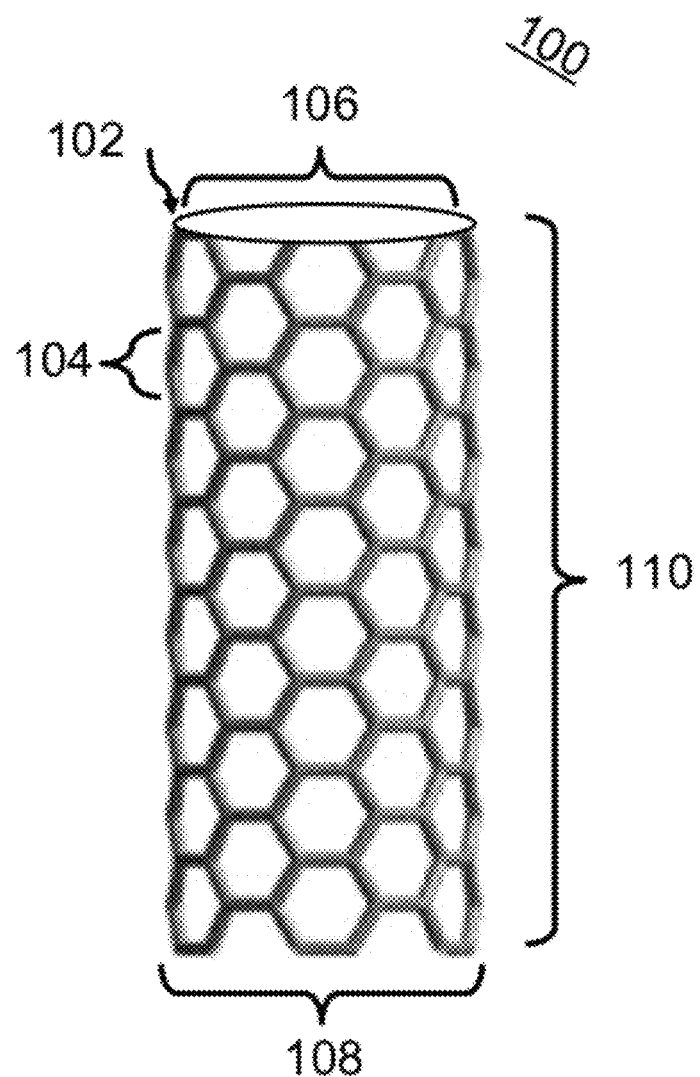
FIG. 1 illustratively depicts an exemplary semipermeable nanotube, in accordance with exemplary embodiments of the present invention.

Generally speaking, the following detailed description is directed to systems and methods for removing impurities from fluid such as blood, for example, by application of electric fields that cause selected charged impurities to be selectively transported to and be captured within semipermeable nanotubes. Once these impurities are contained within the nanotubes, they may be subsequently removed as a stream of waste species. Further, to selectively filter impurities in such fluids, the systems and methods can, amongst other things, utilize surfaces that are coated with molecules having specific functionalities (e.g., anticoagulants), and can incorporate impurity sensors, microprocessors, and/or feedback systems.

By way of example, the systems and methods described here can be used to form an effective blood purification or artificial kidney system suitable for implantation within a human body. This artificial kidney can substantially filter out impurities (e.g., charged impurities) from blood. More specifically, in exemplary embodiments, to filter impurities this artificial kidney system operates by applying an electric field across a collection of one or more semipermeable nanotubes. This applied electric field can selectively transport (e.g., selectively drive) impurities (e.g., ions) in blood flowing outside (and alongside) the semipermeable nanotubes, such that the impurities are preferentially expelled from the flowing blood stream and transported into and/or through the semipermeable nanotubes. These impurities can then form a separate waste stream, while the remaining flowing blood is left with a reduced concentration of impurities. For example, the system and methods disclosed herein can form an artificial kidney system that at least partially separates impurities (e.g., charged impurities) from blood to form two distinct fluid streams. The first flow stream is cleaned, filtered blood (whose impurities have been sent to the inside of the nanotubes). The second flow stream is the wastestream consisting of a solution of those impurities removed from the patient's blood. The advantage of such a system is that since it can operate continuously, impurity removal efficiencies need not be very high. If some impurities are not removed from the bloodstream during a first passthrough, they may be removed from the bloodstream during subsequent passthroughs.

Utilizing such systems and methods to form, by way of example, an implantable artificial kidney system, patients may continue their normal activities while blood purification occurs continuously, silently, and/or autonomously within a patient's body. In some instances, such an artificial kidney system can filter and/or remove impurities without substantial application of external pressures (e.g., such as that used in hemodialysis). Also, in exemplary embodiments, this implantable artificial kidney system can purify blood using the patient's own blood flow and/or blood pressure. Further still, in some instances, the implantable artificial kidney system can purify blood without requiring that a patient's blood be circulated externally and the impurity (e.g., waste species) stream can be excreted through the patient's own bladder.

It will be understood that the disclosed systems and methods can be used for capturing impurities, removing impurities, capturing charged impurities, removing charged impurities, filtering and/or purifying impurities from any type of fluid such as, but not limited to, water, aqueous solutions, non-aqueous solutions, precious material recovery systems, wastewater processing, blood, cerebrospinal fluid, bile, and bio-fluids. In a preferred embodiment, the fluid being filtered and/or purified is blood. However, this embodiment and the following descriptions are in no way meant to be a limitation on the types of fluids that can be purified using the disclosed systems and methods.

It will be understood that the systems and methods disclosed here may be used either internally, for example, as an implantable artificial kidney system; or externally, for example, in a larger external device; or in any combination of internal and external systems. While the systems and methods are described, at times, as an implantable artificial kidney system, artificial kidney system, or the like, that captures impurities, removes impurities, captures charged impurities, removes charged impurities, filters and/or purifies blood, this description is not meant to be a limitation on the configurations that are possible for such systems and methods. Rather, this is merely for ease and is in no way meant to be limiting. Further, it will be understood, that the systems and methods disclosed here may be used with humans and/or any form of animals.

In exemplary embodiments, the systems and methods can be dimensioned and/or fabricated from materials for implantation in the body. For example, any of the components can be made from biocompatible materials. For another example, the dimensions may be selected such that the system can be located within the body, for example, replacing a kidney.

In an exemplary embodiment, the system and methods disclosed utilize nanostructure materials such as, but not limited to, carbon semipermeable nanotubes, inorganic semipermeable nanotubes, DNA semipermeable nanotubes, membrane semipermeable nanotubes, carbon semipermeable nanostructures, inorganic semipermeable nanostructures, DNA semipermeable nanostructures, membrane semipermeable nanostructures, and/or any other form of nanostructure constructed of organic materials, inorganic materials, cross-linked polymers, metals, metal alloys, and any other mixture or combination of suitable, biologically compatible materials and/or any other nanostructure material. For ease, the nanostructure materials are, at times, described as being carbon semipermeable nanotubes, carbon semipermeable nanostructures, or the like. This is merely for ease of reference and is in no way meant to be a limitation.

Further, in exemplary embodiments, the shape of the semipermeable nanostructures can be tubular, cylindrical, cylinder-like, spheroid, ellipsoid, substantially flat, membrane like, and/or any other shape. For ease, the shape of the semipermeable nanostructures is, at times, described as being tubular, cylinder-like, cylindrical semipermeable nanotubes, or the like. This is merely for ease of reference and is in no way meant to be a limitation.

Referring to FIG. 1, in exemplary embodiments, an implantable artificial kidney system can include a plurality of carbon semipermeable nanotubes 100 that typically are formed from rings of carbon atoms linked together in a continuous pattern, forming cylinder-like nanostructures having porous walls 102. Further, pore sizes or openings 104 in these semipermeable nanotubes walls 102 can be large enough to allow water and selected charged impurities (e.g., ions) to pass through. However, they may not be large enough for red blood cells or other large blood constituents to pass through.

In exemplary embodiments, the sizes of pores 104 can be selected to range from a size sufficient to pass various impurities, for example, ions such as, but not limited to, sodium, potassium, and chloride (to name a few) and/or the size of the pores 104 can be selected to range up to that of larger impurities, for example, middle molecular weight molecules that need to be removed by those who suffer from, for example, kidney failure.

Further, in some instances, these semipermeable nanotubes can vary in structure and can be classified either as a single layer (single wall) or a multiple layered (multi-wall) structure, for example, of hexagonal lattice graphite, wrapped into a cylindrical semipermeable nanotube. The term "single" or "multi" refers to how many carbon atom layers make up the sidewalls (e.g., walls 102) of individual semipermeable nanotubes. By way of example, various forms of single-walled semipermeable nanotubes and multi-wall semipermeable nanotubes made by known techniques can be used, such as, but not limited to, These materials, while having been made in various laboratories, are not yet commercially available.

The size of the pores 104 in wall 102 of semipermeable nanotube 100 can be carefully controlled by variations in synthesis parameters. For example, single and multi-walled carbon semipermeable nanotubes with precise pore-structures and pore sizes can be fabricated for removing specific impurities from specific fluids.

Still referring to FIG. 1, in exemplary embodiments, the internal diameter 106 of semipermeable nanotubes 100 can range from about 1 nm (e.g., for single wall semipermeable nanotubes) up to about several nanometers (e.g., for multi-wall semipermeable nanotubes). Such diameters are of the same order of magnitude as the size of most single molecules. More specifically, the dimensions of multi wall semipermeable nanotubes can include an outer diameter 108 of about 10 to 15 nanometers, an inner diameter 106 of about 2 to 6 nanometers, and an overall length 110 of about 0.1 to 10 microns or more.

In exemplary embodiments, semipermeable nanotubes 100 can be several microns long such that their aspect ratio (e.g., length to diameter ratio) can be in excess of 10,000. Comparatively, a single red blood cell has a diameter of about 7,000 nanometers, while a typical virus measures only about 100 nanometers in diameter.

In exemplary embodiments, the carbon semipermeable nanotubes, as discussed herein, can be selected based on variables such as, but not limited to, specific electronic and structural characteristics and/or other variables such as, but not limited to, tubular shape, length to diameter ratios, thermal conductivity, electrical mobility, electrical current capacity, tensile strength, size, compatibility with current semiconductor fabrication processes, ability to be chemically functionalized, and absorption properties toward various compounds, to name a few. These nanostructures may be envisioned as a cage where selected impurity species may be trapped. Once a particular species is trapped or contained within a nanotube, it will not readily be able to leave and return to the original incoming blood stream.

Figure 2:
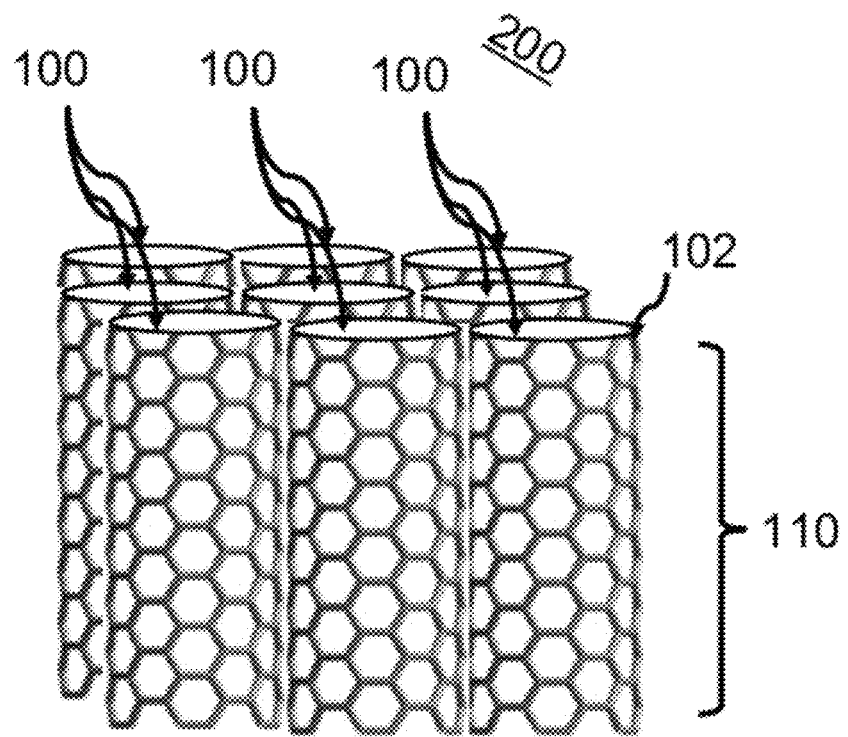
FIG. 2 illustratively depicts an exemplary array and/or collection of individual semipermeable nanotubes, in accordance with exemplary embodiments of the present invention.
Figure 3:
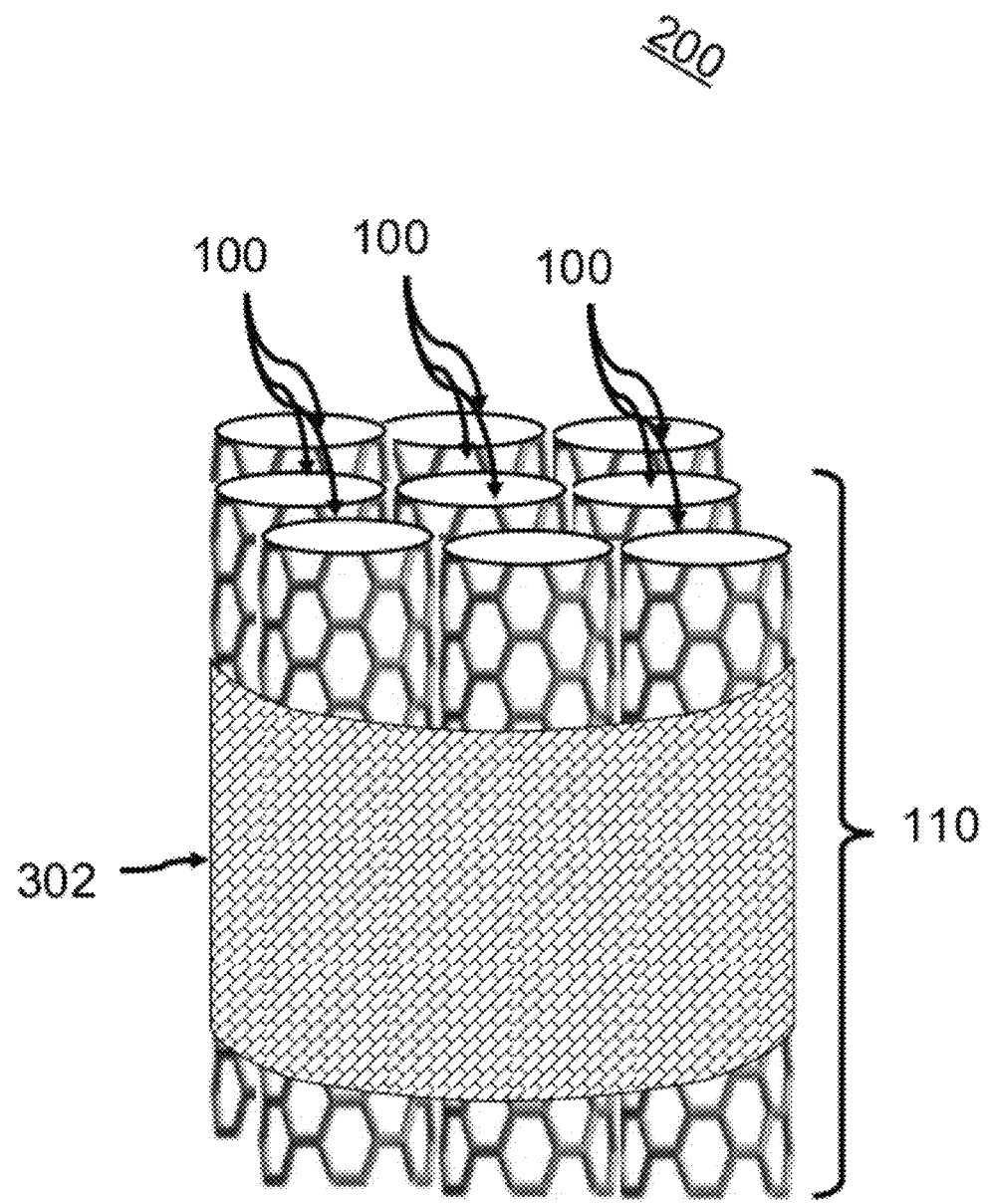
FIG. 3 illustratively depicts an exemplary array and/or collection of individual semipermeable nanotubes in conjunction with an exemplary outer enclosure, in accordance with exemplary embodiments of the present invention.

Referring to FIG. 2 in exemplary embodiments, an array and/or collection of a number of individual semipermeable nanotubes 100 can be assembled closely together along at least some of length 110 of walls 102 to form an array of semipermeable nanotubes 200. In this configuration, the array and/or collection of individual semipermeable nanotubes 100 can be in a substantially parallel assembly, for example, forming a substantially parallel array 200 of nanotubes 100. Such array 200 of semipermeable nanotubes can also be surrounded by and/or held together by, for example, a larger outer enclosure 302, as shown in FIG. 3. Of course, individual semipermeable nanotubes 100 within outer enclosure 302 can be either held together tightly and/or loosely. These nanotubes need not fill the entire inside volume of the outer enclosure.

In exemplary embodiments, outer enclosure 302 may be constructed in a similar fashion as semipermeable nanotubes 100. Alternatively, outer enclosure 302 can, for example, be fabricated from any suitable material such as, but not limited to, silicone rubber, polymers, and/or any suitable semiconductors, to name a few. As described below, outer enclosure 302 essentially serves as a conduit and/or pipe to transport blood or other fluid to be purified.

It will be understood that any number of semipermeable nanotubes 100 and/or outer enclosure 302 can be used for the systems and methods disclosed. For ease, at times only one outer enclosure, one semipermeable nanotube, and/or only a few semipermeable nanotubes are disclosed. This is merely for ease and is in no way meant to be a limitation.

Figure 4:
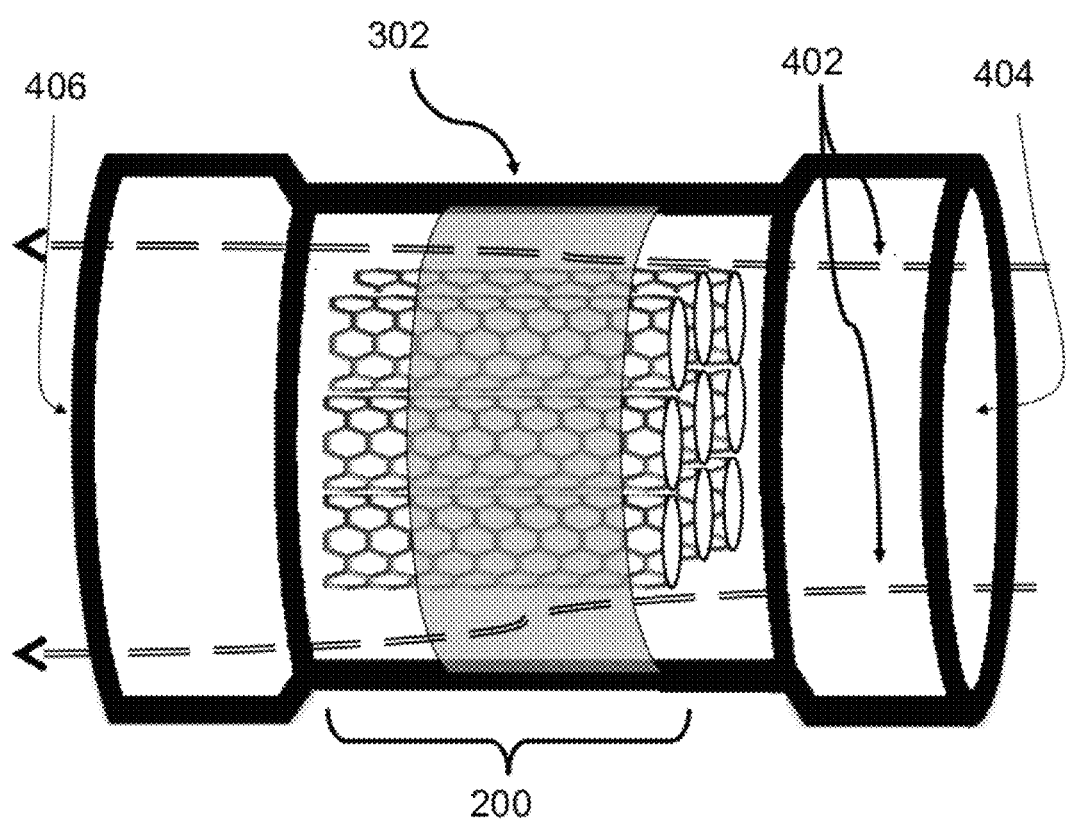
FIG. 4 illustratively depicts a fluid flow traversing a plurality of individual semipermeable nanotubes and/or outer enclosure, in accordance with exemplary embodiments of the present invention.

Referring to FIG. 4, in exemplary embodiments, blood 402 to be purified enters outer enclosure 302, via inlet 404, and flows alongside and parallel to the length 110 of at least some of the semipermeable nanotubes 100 in the array 200, such that purified blood 402 exits, via outlet 406, at the outflow end of outer enclosure 302. To purify blood 402, in an exemplary embodiment, this implantable artificial kidney system utilizes controlled application of either a continuous and/or modulated electric fields across individual semipermeable nanotubes 100 and/or semipermeable nanotube array 200 to assist in mono-directional transport and diffusion of selected impurity species through the walls of the semipermeable nanotubes 200.

Mono-directional transport and diffusion of selected impurity species (e.g., ions) through the walls 102 of semipermeable nanotubes 100 and/or semipermeable nanotube array 200 can be achieved, for example, by depositing and/or coating electrically conducting or semiconducting contacts on opposite sides of outer enclosure 302, or semipermeable nanotubes 100, and/or semipermeable nanotube arrays 200 to which appropriate voltages can be applied. If chirally prepared semipermeable nanotubes 100 have sufficient electrical conductivity, there may be no need for and/or a substantially reduced need for supplying conducting or semiconducting contacts to the semipermeable nanotubes 100.

When the outer enclosure 302 (e.g., holding the array semipermeable nanotubes together) is electrified by applying appropriate voltage potentials across its walls, impurities (e.g., ions) dissolved in the fluid flowing within the outer enclosure will exhibit an enhanced transport profile, causing these impurities to travel across and/or through the individual porous semipermeable nanotube walls. The driving force for impurities removal (e.g., ion removal) is therefore no longer limited to hydrostatic pressure, as it would be in typical dialysis systems. Rather, impurity species within the fluid (e.g., travelling externally, parallel and alongside the semipermeable nanotube walls, may be selectively transported across the semipermeable nanotube walls via such field induced transport. By way of example, by applying selected voltage potentials across the semipermeable nanotube walls, impurities (e.g., selected ions) in solution outside the semipermeable nanotube walls can have increased mobility to transport into and through the semipermeable nanotube walls. Thus, as the incoming fluid (blood) travels along the length of the outer enclosure 302, the applied electric field will preferentially drive some of the contained impurities into the nanotube "cage" within the center of this enclosure.

In exemplary embodiments, an electric field is formed by the application of a voltage across an entire collection of individual semipermeable nanotubes and/or across at least some of these individual semipermeable nanotubes. The electric field can be oriented at an angle (e.g., substantially perpendicular) to the semipermeable nanotube's length (i.e., across the semipermeable nanotube walls). This applied electric field can drive dissolved charged impurities (e.g., dissolved impurity ions) in the flowing blood (e.g., flowing outside the semipermeable nanotubes) causing them to be preferentially expelled from the flowing blood and directed into the semipermeable nanotubes. Once these impurities are contained within these nanotubes, they will essentially remain trapped within the nanotube structure and form a separate waste stream of water and dissolved impurities. This waste stream containing dissolved impurities removed from the flowing blood can now be transported within the porous semipermeable nanotubes to form a separate waste stream, while the blood flowing outside the collection of nanotubes is left with lower concentration of impurity species and is thereby purified.

Figure 5:
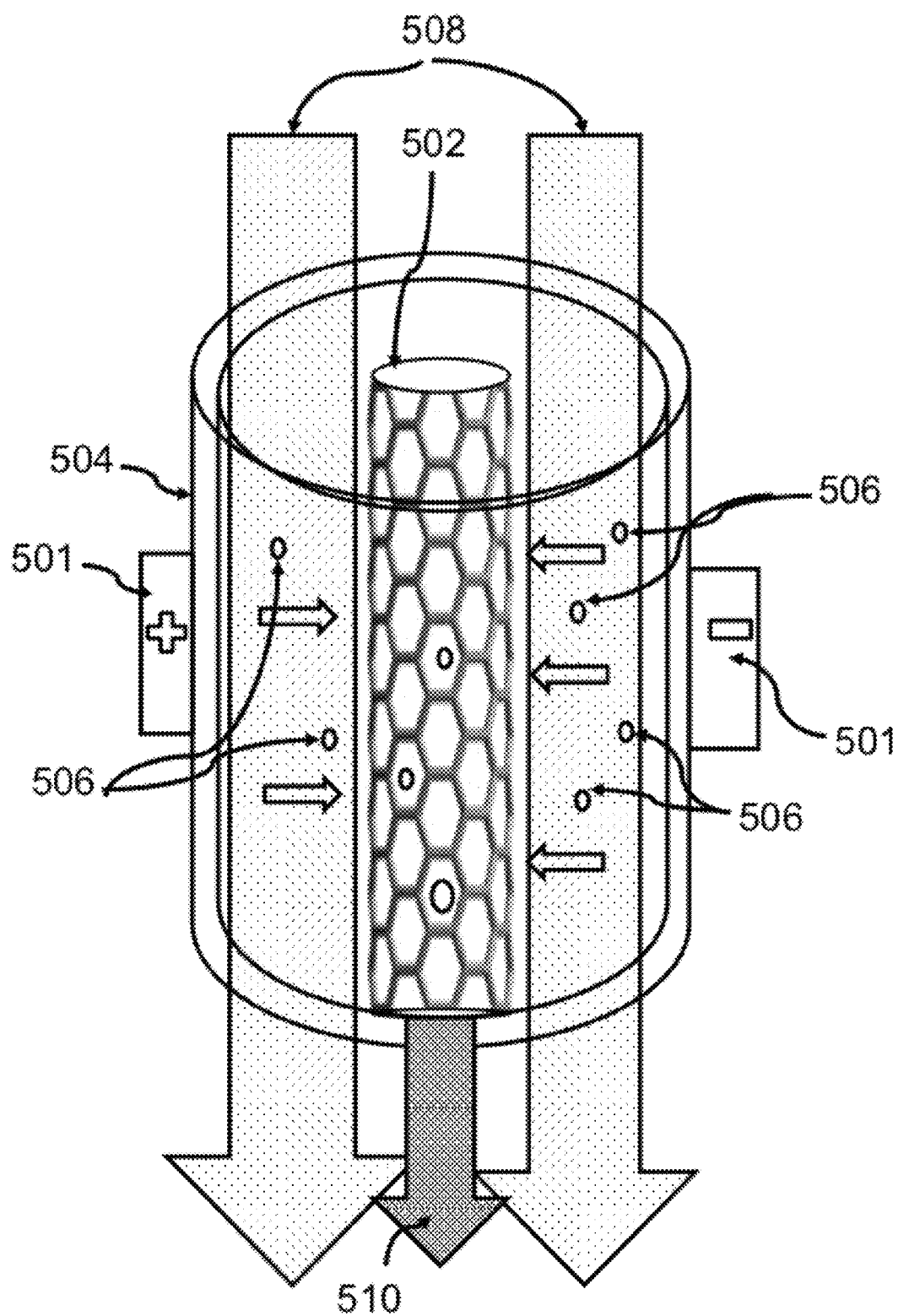
FIG. 5 illustratively depicts a single semipermeable nanotube in the center of an outer enclosure with an electric field gradient being applied across the entire assembly such that impurities present in a flowing bloodstream can be selectively transported out of the bloodstream and into the central semipermeable nanotube, in accordance with exemplary embodiments of the present invention.

By way of example, FIG. 5 illustrates a single semipermeable nanotube 502 in the center of an outer enclosure 504 with an electric field being applied, for example, by a voltage source (e.g., electrodes 501). With this arrangement, various charged impurities 506 may be selectively transported out of blood flow 508 and into the semipermeable nanotube 502 wherein they remain captured and/or form a new waste species flow stream 510 composed of the separated impurities, possibly including their hydration layers.

Figure 6:
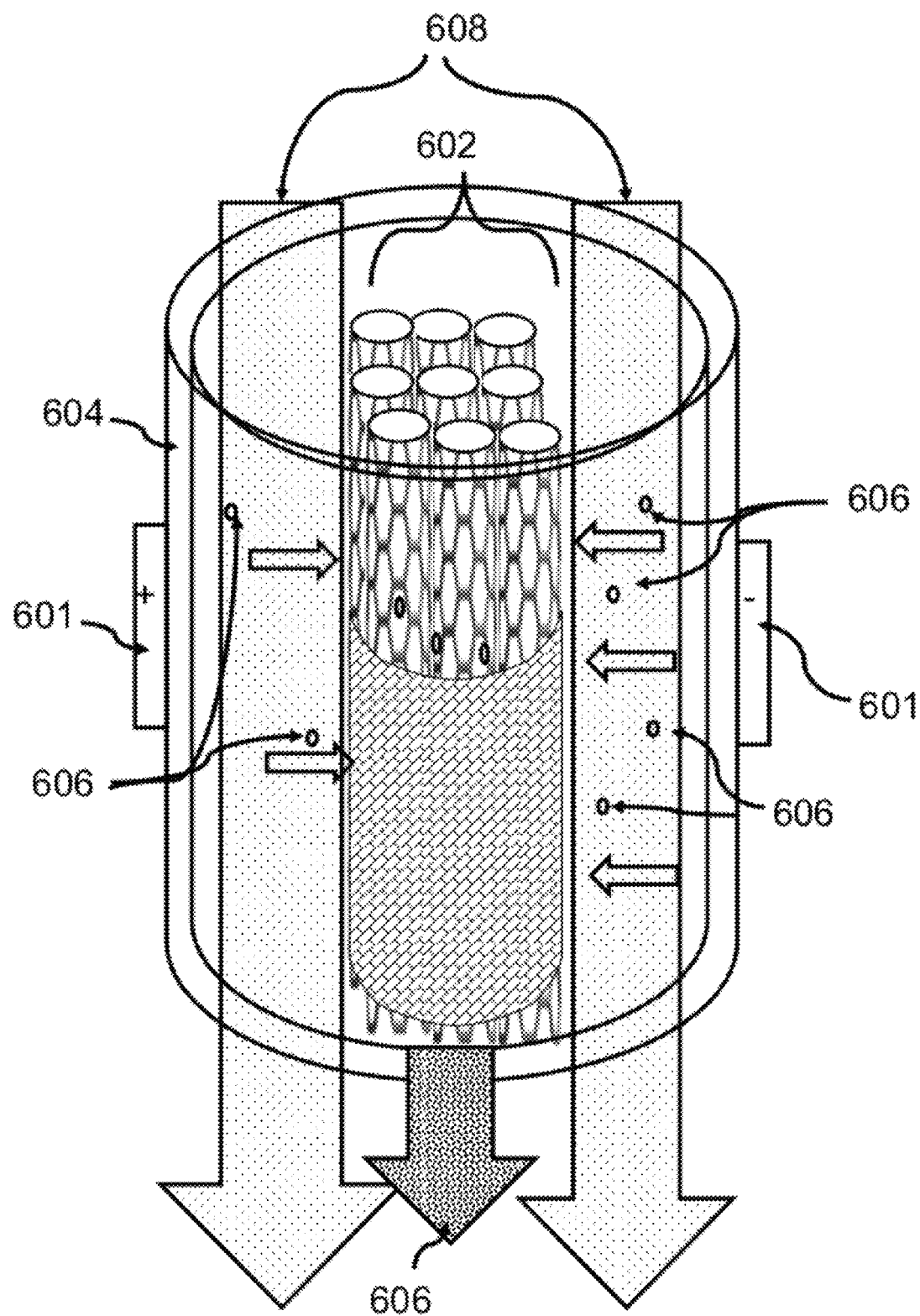
FIG. 6 illustratively depicts a plurality of semipermeable nanotubes in the center of an outer enclosure with an electric field gradient being applied across the entire assembly such that impurities present in a flowing bloodstream can be selectively transported out of the bloodstream and into the semipermeable nanotubes, in accordance with exemplary embodiments of the present invention.

By way of another example, referring to FIG. 6, an array of semipermeable nanotubes 602 are illustratively depicted in an outer enclosure 604 wherein incoming blood flow 608 passes through the outer enclosure 604 while none of blood flow 608 passes through the array of semipermeable nanotubes 602. This is because the openings in the nanotubes are too small to allow blood to flow through them. Due to the action of the applied electric fields (generated by electrodes 601) on the blood flow, the array of semipermeable nanotubes 602 collects the unwanted charged impurities and/or associated water 606 expelled from the blood flow 608.

In exemplary embodiments, the diameters of the semipermeable nanotubes and/or applied voltages used can be regulated such that, for example, only a few millivolts can generate substantially large electric fields when applied across nanotube-sized dimensions. For example, applying 0.001V across a 10 nanometer cylinder can generate effective electric field strengths of about 1000 V/cm.

Since charged species generally also carry with them hydration shells of attached water molecules, as charged species transport across the semipermeable nanotube walls, water molecules may simultaneously travel with them. This can have the effect of decreasing water levels (osmolarity) within the blood being purified. As will be described later, water levels in the patient's blood may be continuously monitored while the applied electric fields are regulated to optimize impurity removal while minimizing water removal.

As described, the artificial kidney system can control transfer rates of impurities across nanotube membrane walls by, for example, controlling electrical potentials applied across these semipermeable nanotubes. This field-induced effect can be scaled directly with semipermeable nanotube surface areas (i.e., the square of semipermeable nanotube diameter). For example, an artificial kidney system utilizing smaller diameter semipermeable nanotubes can operate with reduced applied potentials.

Applied potentials across these semipermeable nanotube walls need not be constant. For example, this artificial kidney system can be arranged to dynamically adjust applied voltages in accordance with the particular charged species to be removed, its concentration, as well as the presence/concentrations of other charged species in the bloodstream. In exemplary embodiments this artificial kidney system may utilize suitable voltage waveforms such as, but not limited to, pulsed, or sinusoidal. Other suitable voltage waveforms and/or voltage profiles (e.g., duty cycles) can be used depending on the particular application.

In exemplary embodiments, electrical potentials applied across the semipermeable nanotubes can be provided by a battery or other suitable voltage sources, including sources powered by the human body such as auto-bio-fuel cells and the like.

In exemplary embodiments, the artificial kidney system can include an encasement that can be constructed of any biocompatible material such as, but not limited to, implant grade plastics, stainless steel, titanium, and/or any other biocompatible material. Further, in exemplary embodiments, the implantable artificial kidney system can utilize semipermeable nanotubes and/or other materials that have been functionalized with specifically selected surfactants and/or anticoagulants selected to prevent blood that contacts their surfaces) from coagulating or clotting.

As used herein, "functionalized" (or any version thereof) refers to surface treatments by which specific atomic molecular groups may be attached to alter specific properties of semipermeable nanotubes or structures described herein. Functionalization can be generally performed by various surface modification techniques such as wet chemistry, or vapor, gas, and/or plasma chemistry, and microwave assisted chemical techniques, to name a few. These techniques utilize surface chemistry to bond desirable materials to surfaces of carbon semipermeable nanotubes. Similar techniques may be used to modify other materials as well. For example, known methods can be used to "activate" the carbon semipermeable nanotubes, for example by breaking at least some of C—C or C-heteroatom bonds, thereby providing a surface for subsequently attaching specific molecules or molecular clusters thereto. Functionalized carbon semipermeable nanotubes can include chemical groups, such as, but not limited to, carboxyl groups, that can be attached to surfaces, such as the external surface, of the carbon semipermeable nanotubes. Semipermeable nanotube functionalization can occur through a multistep procedure by which functional groups can be sequentially added to a semipermeable nanotube wall to arrive at specific, desired properties.

For example, by attaching anticoagulant species specifically to those surfaces that directly contact flowing blood, clotting of blood passing near these surfaces can be prevented and/or substantially reduced. Surfaces to be coated with anticoagulants can include, but are not limited to, the outer facing surfaces of the porous semipermeable nanotubes 100 and/or the inner facing surfaces of outer enclosure 302. By way of example, anticoagulants such as Hirudin or Heparin can be bound to outside walls of the carbon semipermeable nanotubes 100 or to the inner walls of the outer enclosure 302 using known techniques, i.e., where surfaces in the disclosed embodiments would contact blood as it passes through the outer enclosure 302. In this way, once blood is flowing through the device, its tendency to clot will be reduced. The inside portion of the nanotubes need not be coated with anticoagulants since no blood per se will be present there. The inner portion of the nanotubes will generally only contain dissolved impurity species.

In exemplary embodiments, an implantable artificial kidney system can utilize selected anticoagulants, for example, applied to surfaces that contact the blood to substantially reduce and/or eliminate problems associated with systemic administration of anticoagulants to patients during kidney dialysis. Binding anticoagulants to a specific filtration device directly at the point where it may be needed, rather than traditionally administered systemic delivery, should substantially reduce possible side effects and/or the associated inconvenience of administering anticoagulant drugs.

Further, the implantable artificial kidney system can utilize the attaching of anticoagulants to semipermeable nanotubes such that these molecules act as a barrier, substantially preventing large proteins from entering and/or clogging the semipermeable nanotube pores. As noted, in the exemplary embodiments, only those portions of the device that actually contact blood need be coated with anticoagulants. This means that only the inner walls of the outer enclosure 302 (carrying the to-be-filtered blood) and/or the outer walls of the semipermeable nanotubes 100 that also come into contact with blood, require attachment of anticoagulants.

In exemplary embodiments, the implantable artificial kidney system can attach polymers, anticoagulants, and/or other selected molecules to outer nanotube walls (and/or any other surface of the semipermeable nanotubes and/or outer enclosure).

Anticoagulant molecules (e.g., similar to Heparin or Hirudin) may also be covalently linked onto carbon scaffolds of semipermeable nanotube sidewalls using such known techniques. Once so attached, these anticoagulant molecules can also help substantially prevent blood from clotting. For example, anticoagulants may be coated on the inside of outer enclosure 302 and/or the outside surfaces of the semipermeable nanotubes 100.

In exemplary embodiments, the quantity and type of anticoagulant utilized in the implantable artificial kidney system can be predicated on variables, such as, but not limited to, blood flow rates, surface area of the semipermeable nanotube surfaces, and the space between the semipermeable nanotubes in the enclosure, with enough area covered to substantially prevent exposed areas, which could be a nidus for clot formation. In the event that the material surrounding the nanotubes is not easily directly functionalized with anticoagulants, an additional, more easy functionalized, inner layer may be added. Functionalization of the inner facing walls of the outer enclosure (e.g., carrying blood) can be achieved by numerous known techniques (e.g., depending on the enclosure composition), such as, but not limited to as covering with planar sheets of functionalized carbon nanotube structures or fullerines.

In exemplary embodiments, this implantable artificial kidney system can also utilize substantially small, substantially lightweight, sensors that are specific to certain impurities. This would allow for example, the ability to measure concentrations of selected charged species within either the incoming blood, within the already purified blood, and/or both. Such sensors may include impurities-specific sensors, ion-specific electrochemical sensors, spectroscopic type sensors, which can communicate signals to suitable microcontrollers.

In a further exemplary embodiment, the sensors can measure concentrations of selected charged species in either incoming fluids (before filtration) and/or outgoing fluid (after filtration). This information, when coupled to appropriate feedback mechanisms, will allow regulation of applied potentials across individual semipermeable nanotubes and/or suitable collection of semipermeable nanotubes. By way of example, the general types of sensors that can be utilized by the implantable artificial kidney system can include, but are not limited to, sensors that can rapidly detect multiple species such as, but not limited to, Na+ (aqueous) and K+ (aqueous) simultaneously.

This implantable artificial kidney system may also include any number of in-situ detection and/or measurement systems such as, but not limited to, electrochemical detection and/or measurement systems, or optical detection and/or measurement systems (e.g., Raman spectroscopy, visible laser spectroscopy, Attenuated Total Reflection ("ATR")), and combinations thereof. By way of example, ATR spectroscopy, a noninvasive spectroscopic technique, may be used to detect and/or monitor concentrations of selected species in aqueous solution. Utilizing ATR spectroscopy, the reflection of selected electromagnetic wavelengths from a fluid in contact with an optical surface can be detected and monitored. Contact of blood at this surface can provide rapid measurement of the concentrations of a host of selected species in the blood.

In exemplary embodiments, the implantable artificial kidney system can utilize a variety of sensors that can be, for example, non-degradable, non-destructive, non-thermogenic, and/or have a substantially rapid and accurate detection response. Further, the sensors can be designed to communicate their information to a microprocessor for evaluation and response.

By way of example, the implantable artificial kidney system can utilize sensors, microprocessors, and/or other devices to control and/or provide feedback of applied transmembrane potentials utilizing technologies similar to those used with, for example, pacemakers and spinal cord stimulators.

In exemplary embodiments, an implantable artificial kidney system can utilize the techniques disclosed herein to improve blood filtration of selected impurities based on concentration and removal rates (e.g., selected ion concentrations and ion removal rates), by regulated, as directed and/or controlled by a microprocessor that can control voltage source(s) during blood purification by, for example, varying applied potentials and/or their applied duty cycles. The applied potentials can be varied based on information obtained from a number of sensors, such as sensors that can monitor urine flow and/or various impurities concentrations. The sensors can be utilized to substantially avoid patient dehydration, substantially reduce the risk of hyper-osmolarity or hypo-osmolarity, substantially reduce the risk of excessive loss of critical electrolytes, and/or substantially reduce numerous other risks which can be related to the functionality of the artificial kidney system and/or the patient. For example, as impurities are depleted from the blood, it may be important to monitor changes in osmotic pressure and ionic conductivity of the blood, to name but a few parameters. Such changes can affect required electric fields necessary to optimally drive impurities effectively across the porous semipermeable nanotube walls.

To provide such monitoring and control the implantable artificial kidney system can utilize microprocessor-controlled feedback mechanisms coupled with the foregoing sensors to sense changes and make appropriate adjustments to electrical potentials applied across semipermeable nanotube arrays. For example, the implantable artificial kidney system can include feedback mechanisms from one or more sensors situated in any number of locations to carefully monitor and/or provide feedback on concentrations of selected species within the blood. Regions that can be selected for sensing may include but are not limited to, afferent and effluent parts of the blood flow, inflow and outflow sites within the device, or more distal locations.

The blood flow rate through this purification device is essentially fixed and controlled by the patient's own blood flow rate. The one parameter that may be modified is the charged species removal rate. This is based on applied potentials across the flowing blood. Based on measured concentrations from the various sensors, a microprocessor can control and/or regulate applied potentials across the outer enclosure 302 containing the collection of individual semipermeable nanotubes 100. For example, if impurities concentrations in the effluent are sufficiently low, implying that the patient's blood in relatively free of impurities further blood purification rates may be substantially decreased and/or stopped by lowering applied voltages across these semipermeable nanotubes. If impurities and/or undesirable charged species concentrations in the incoming blood are high, implying that the patient's blood still requires treatment and additional impurity removal, applied potentials can be substantially increased and/or otherwise appropriately altered to increase transport across the nanotube walls rates (e.g., ion transport), thereby increasing purification rates.

In exemplary embodiments, the implantable artificial kidney system allows removal of selected species from contaminated blood/plasma based on continuous, tangential-flow purification by optimizing transport rates in accordance with both the size and the charge of target impurities to be removed from blood. Further, the implantable artificial kidney system performs blood purification by, for example, the combination of applied electrical potentials and semipermeable nanotube fabrication technology. The size of the pores in the semipermeable nanotube walls can be further tailored to allow more facile transport of selected molecular charges and sizes, ranging from the molecular size of ions such as sodium, potassium, calcium, chloride for example, to the size of the largest middle molecular weight impurity molecules that may need to be removed during dialysis, (e.g., 60 kilo Daltons)).

The artificial kidney blood filtration system can be constructed of two or more concentric semipermeable nanotubes, for example, a dual, coaxial structure constructed as concentric semipermeable nanotubes. Further still, a slightly larger, outer enclosure or sleeve can surround the numerous smaller, semi porous, semipermeable nanotubes and, in some instances, this outer enclosure can act as a conduit for blood to be purified.

As noted above, pore sizes of the semipermeable nanotube walls can be constructed so that selected impurity species can be readily pass through while larger molecules can be excluded. The size and pore sizes of the individual nanotubes within a given assembly need not be the same. A range of nanotube sizes may be combined to achieve optimum performance. In exemplary embodiments, a plurality of varying semipermeable nanotube types (e.g., adjacent to each other within the array) can be constructed so that their outer walls have selected openings of different sized pores or a selected distribution of openings. With this arrangement, specific impurities can preferentially pass through these openings thereby enabling the transport of a substantially wide range of desired charged species.

In exemplary embodiments, as selected impurities are transported through the semipermeable nanotube walls and into the inner nanotubes, this growing collection of waste species together with their aqueous hydration layers (e.g., water) can constitute a separate waste stream that can travel through the inner semipermeable nanotubes and be eventually expelled from the body after collection in a common outlet which is connected to the resident patient ureter. In some instances, the waste stream can be a function of other variables such as, but not limited to, the patient's blood flow rate through the outer enclosure, the electric potentials that are effectively driving impurities across the nanotubes walls and other reasonable variables that may affect the waste stream.

In exemplary embodiments, the implantable artificial kidney system can utilizes a plurality of flow streams to purify blood. By way of example, the implantable artificial kidney system utilize three process flow streams: (1) a first stream consists of the incoming flow of unfiltered blood into and through a larger outer enclosure. Following purification, two new flow streams are formed. The first is the waste stream that flows within the nanotube(s) and contains outgoing waste species and/or water that has been removed from the blood under the influence of applied electrical potentials. The second flow stream contains outgoing, cleansed, blood from which impurities have been substantially removed. As described herein, the cleansing process occurs by having this first incoming blood stream contact the inner semipermeable nanotube walls, and, by virtue of applied electric potentials, unwanted species can be selectively transported through the walls of the inner porous semipermeable nanotubes and into the inner semipermeable nanotubes.

In this manner, waste species removed from the blood stream can flow through the inner semipermeable nanotubes to, for example, a collection region that can surround the end of the collection of semipermeable nanotubes in a sealed manner, preventing back leakage in to the cleansed blood stream. The collection regions of the various semipermeable nanotubes can converge with one another into a common collection area be expelled from a separate exit port. This exit port can be connected to the patient's ureter and hence to the patient's bladder wherein the waste stream can be substantially naturally expelled. In operation, this process can preferably occur continuously and/or without requiring that blood be rerouted outside the patient's body.

The outgoing, cleansed, blood from which impurities have been removed can leave the outer enclosure and be routed back to the patient's own bloodstream. For example, because this purification process occurs continuously, and blood can be recycled through the artificial kidney system multiple times, a substantially large number of purification passes can occur. Each single pass of the blood through the artificial kidney system may therefore only be required to remove a small amount of impurities. Following this cleansing process, blood and contained plasma can be rerouted and/or returned to the patient.

In exemplary embodiments, the implantable artificial kidney system can utilize a group of individual semipermeable nanotubes (e.g., where each semipermeable nanotube can be aligned substantially parallel to the flow of blood and also substantially parallel to each other) contained within one enclosure. This array, cluster, or "pod" of semipermeable nanotubes can be used as a substantially parallel filtration system to increase surface area and overall efficiencies of impurity removal. This collection of semipermeable nanotubes can consist of a collection of similar types of semipermeable nanotubes bundled together with a variety of pore sizes to substantially increase the removal efficiency of unwanted charged species. Alternatively, the collection of semipermeable nanotubes can consist of a collection of different types of semipermeable nanotubes, for example, wherein individual or various pluralities of semipermeable nanotubes include varying characteristic pore size distribution.

When an electrical potential is applied across the outer enclosure, all or at least some of the individual semipermeable nanotubes contained within this larger enclosure can become polarized. This means that an electric field is formed across the walls of the nanotubes. The resulting net electric field applied across the collection of individual porous semipermeable nanotube walls in effect can act as a larger surface area filter and provide for a more efficient filtration as blood travels next to them.

Figure 7:
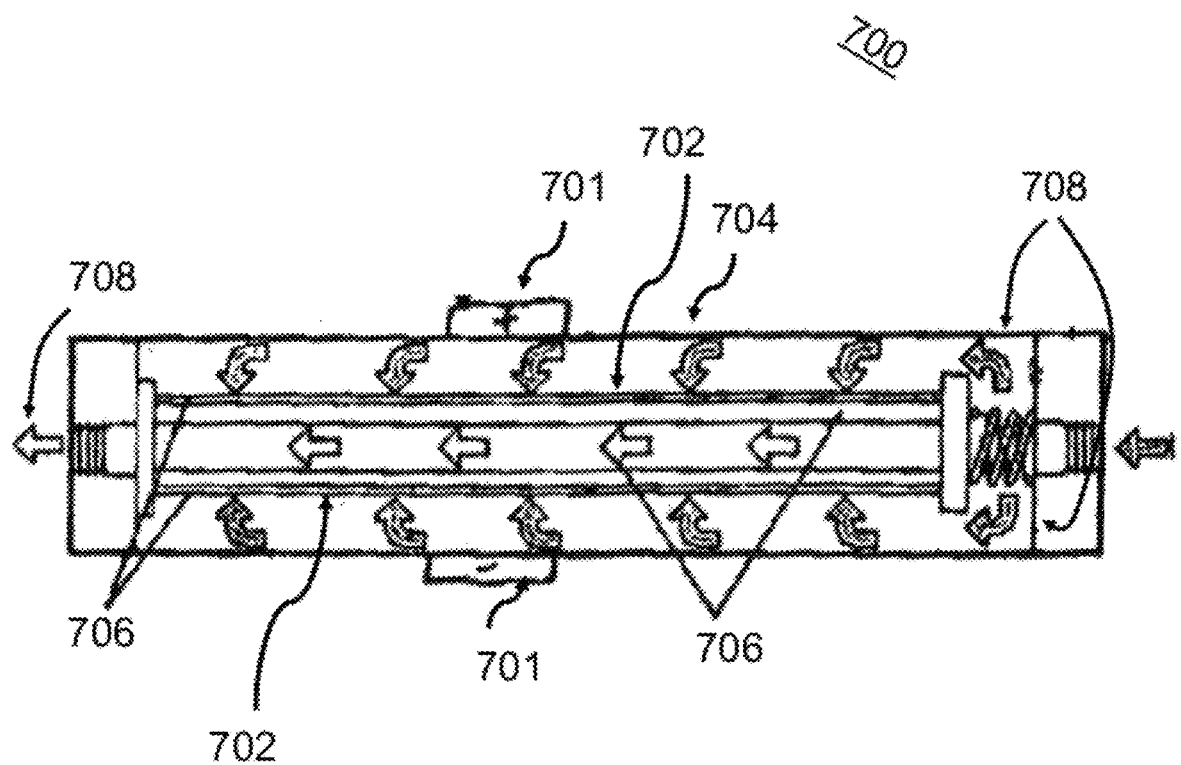
FIG. 7 illustratively depicts impurities being selectively transported out of a bloodstream and into a single semipermeable nanotube, in accordance with exemplary embodiments of the present invention.

Referring to FIG. 7, an exemplary implantable artificial kidney system 700 is schematically depicted with a single semipermeable nanotube 702 structure positioned within an outer enclosure 704. Electrodes 701 are attached to outer enclosure 704. In this configuration, blood flowing 708 within outer enclosure 704 contacts the outside walls of the central semipermeable nanotube 702. Since an electric field is applied via electrodes 701, purified blood exits from the left side while the inner center semipermeable nanotube 902 captures the unwanted charged species 702 rejected from blood 708 via electric fields.

It will be understood that the cross-sectional shape of the semipermeable nanotubes can be any suitable shape such as, but not limited to, elliptical, conical, spherical, hyperbolic, or any combination, of other reasonable shapes. For ease, the cross-sectional shape of the semipermeable nanotubes is described herein, as being round. This is merely for ease of reference and is in no way meant to be a limitation.

Figure 8:
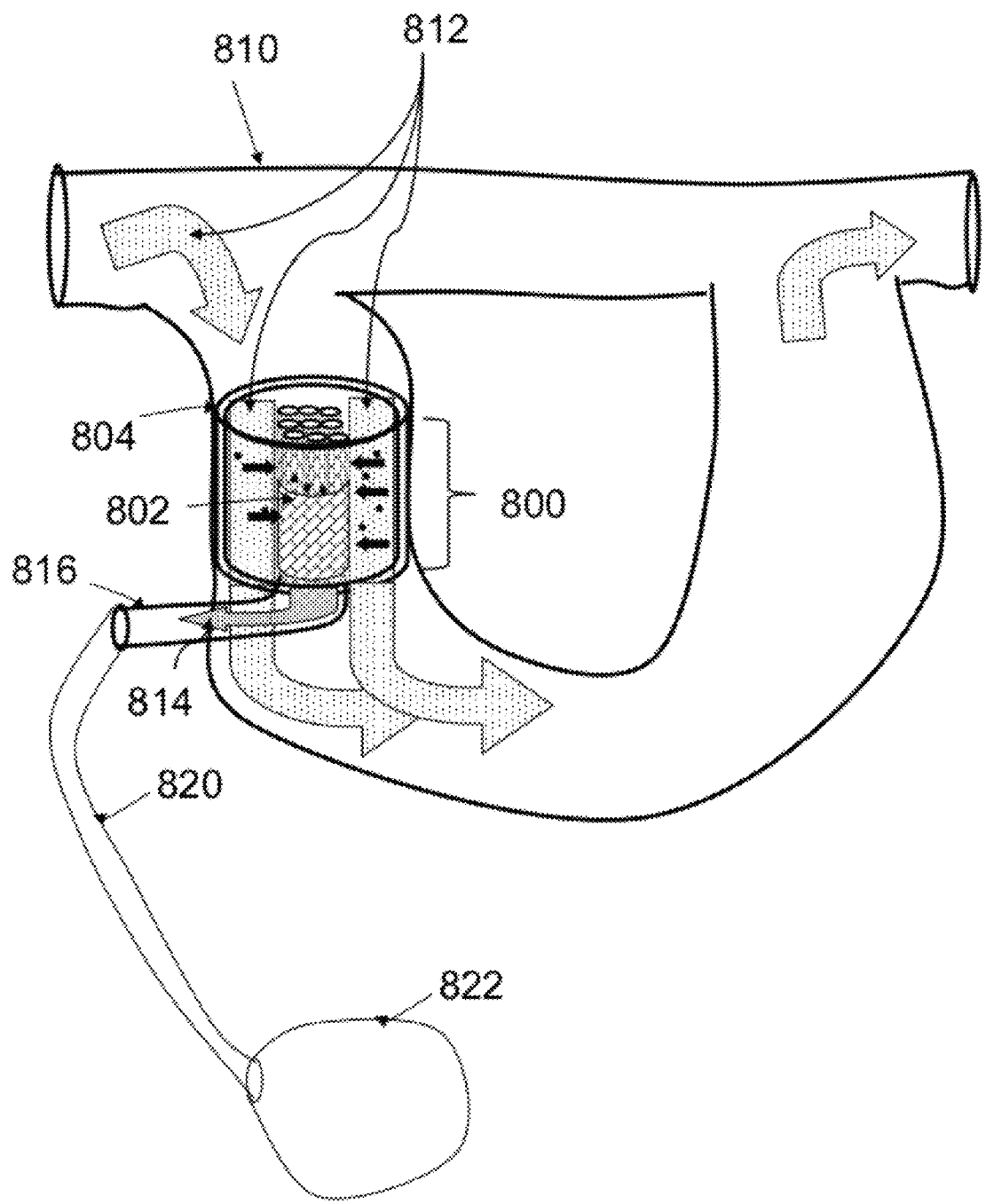
FIG. 8 illustratively depicts an exemplary artificial kidney system that can be attached as a shunt to a blood vessel, in accordance with exemplary embodiments of the present invention.

Referring to FIG. 8, in exemplary embodiments, the implantable artificial kidney system 800 can include a pod 802 and/or collection of semipermeable nanotubes within an outer enclosure 804 that can be attached as a shunt to a blood vessel 810. By way of example, a given blood vessel (e.g., artery or vein) can be tapped as the source of blood for this purification device. Following purification, the blood 812 may be redirected back to either the same blood vessel or to a different one. Further, the unwanted impurities (wastestream) 814 rejected from blood 812 may be redirected separately, for example, out of the body and/or merged into a ureter for excretion. In exemplary embodiments, the unwanted impurities (wastestream) 814 rejected from blood 812 may be redirected separately, into a tubular structure 816 which can attach, for example, to ureter 820 leading to bladder 822 and/or can attach directly to bladder 822.

Further, a collection of semipermeable nanotubes within an outer enclosure can be constructed such that they included flared ends. The entire device can then be connected at both flared ends, for example, to ease securing it to blood vessels at both ingress and egress points.

The maximum fluid filtration rate (e.g., the rate at which charged species can be driven into and through the inner semipermeable nanotube pores) and waste removal efficiencies will generally be a function of the potential applied across the semipermeable nanotubes.

By way of summary, the systems and methods described herein utilize semipermeable nanotube structures in conjunction with the application of carefully controlled electrical potentials across the walls of these semipermeable nanotube structures to selectively transport (e.g., selectively drive) impurities thereby separate them from a fluid stream (e.g., blood). Selected impurities, together with their water of hydration removed from flowing blood can be gathered within the individual semipermeable nanotube structures to form a waste stream. The collection of individual semipermeable nanotubes carrying this waste stream, may be combined and merged into a waste stream outlet which could be attached to the extant ureter in a similar fashion to the attachment made with arteries or veins. By way of example, if the ureter is attached to the exit port of the collection of semipermeable nanotubes, it can be attached in its natural fashion to the bladder and effluent waste stream fluid can be removed as urine, in a manner substantially similar to a normal kidney and/or genitor urinary system. Sensors for various impurities and chemicals of interest can be added to feed back information to a microprocessor to monitor constituent concentrations in the effluent, and control the applied potentials.

Now that exemplary embodiments of the present disclosure have been shown and described in detail, various modifications and improvements thereon will become readily apparent to those skilled in the art, all of which are intended to be covered by the following claims.

What is claimed is:

1. An artificial kidney system for removing impurities from a bodily fluid, comprising:
    at least one semipermeable nanotube assembly including a plurality of semipermeable nanotubes assembled to form an array, the plurality of semipermeable nanotubes forming the array being aligned substantially in parallel, said array defining a first longitudinal axis along the lengths of the nanotubes, each of said nanotubes including a lumen and nanotube walls, each of said nanotube walls having a plurality of pores;
    an enclosure containing the at least one semipermeable nanotube assembly, an inlet, and an outlet, the enclosure comprising a second longitudinal axis and providing a fluid path from the inlet to the outlet through which at least some of the bodily fluid may flow, the fluid path extending alongside the first and second longitudinal axes and external to the at least one semipermeable nanotube assembly; and
    electrodes coupled to the enclosure, wherein the electrodes generate an electric field oriented across the first and second longitudinal axes to drive at least some of the impurities of the bodily fluid in the fluid path through the plurality of pores in the nanotube walls into at least one lumen of the nanotubes to form a waste stream within the array and along the first longitudinal axis the waste stream removing the impurities from the bodily fluid,
    wherein the artificial kidney system is dimensioned to be implanted within a body.

2. The artificial kidney system of claim 1, wherein the bodily fluid is blood.

3. The artificial kidney system of claim 1, wherein at least some of the impurities removed from the bodily fluid are also at least one of (i) captured within the at least one semipermeable nanotube assembly; (ii) removed from the system as the waste stream: and (iii) removed from the system as the waste stream flowing to the body's ureter.

4. The artificial kidney system of claim 1, further comprising:
    at least one sensor for monitoring an amount of at least one of the impurities within the bodily fluid.

5. The artificial kidney system of claim 4, further comprising:
    at least one microprocessor that regulates the electric field by analyzing information obtained from the at least one sensor.

6. The artificial kidney system of claim 5, wherein the electric field is generated by either a fixed or variable voltage waveform.

7. The artificial kidney system of claim 5, wherein the at least one microprocessor utilizes the at least one sensor to adjust the electric field in accordance with a monitored impurity level.

8. The artificial kidney system of claim 4, wherein the at least one sensor utilizes at least one of electrochemical and optical detection.

9. The artificial kidney system of claim 1, further being configured for connection to the body so that the bodily fluid enters the system from at least one of an artery and a vein in the body, the waste stream exits the system for excretion by the body, and the remaining bodily fluid in the system is recirculated through at least one of the same artery, a different artery, the same vein, and a different vein of the body.

10. The artificial kidney system of claim 1, further comprising an energy source that is at least one of (i) an implantable battery and (ii) a biological fuel cell that is configured to utilize glucose potential gradients normally occurring in blood.

11. The artificial kidney system of claim 1, wherein the at least one semipermeable nanotube assembly is constructed from materials comprising at least one of carbon, polymers, cross-linked polymers, inorganic compounds, metals, or organic compounds.

12. The artificial kidney system of claim 1, wherein one or more anticoagulants are attached to one or more surfaces of the system that contact the bodily fluid.

13. The artificial kidney system of claim 1, wherein the plurality of pores are dimensioned to pass water and impurities while red blood cells or other large blood constituents are excluded.

* * * * *